(12) United States Patent
Barshad et al.

(10) Patent No.: US 6,204,919 B1
(45) Date of Patent: Mar. 20, 2001

(54) DOUBLE BEAM SPECTROMETER

(75) Inventors: Yoav Barshad; Yael Barshad, both of Arnheim (NL)

(73) Assignee: NovaChem BV (NL)

( * ) Notice: Subject to any disclaimer, the term of this patent is extended or adjusted under 35 U.S.C. 154(b) by 0 days.

(21) Appl. No.: 08/096,106

(22) Filed: Jul. 22, 1993

(51) Int. Cl.[7] .................................................. G01J 3/28
(52) U.S. Cl. ............................................................ 356/326
(58) Field of Search .................................... 356/319, 326, 356/328, 330–334

(56) References Cited

U.S. PATENT DOCUMENTS

| | | |
|---|---|---|
| 3,385,160 | 5/1968 | Dawson et al. |
| 3,447,873 | 6/1969 | Ashley et al. |
| 3,486,822 | 12/1969 | Harris . |
| 3,637,310 | 1/1972 | Naono . |
| 4,070,111 | 1/1978 | Harrick . |
| 4,164,373 | 8/1979 | Schuss et al. ........................ 356/316 |
| 4,180,327 | 12/1979 | Maeda et al. ........................ 356/320 |
| 4,225,233 | 9/1980 | Ogan ................................... 356/308 |
| 4,245,911 | 1/1981 | Steinbrenner ....................... 356/328 |
| 4,264,205 | 4/1981 | Landa ................................. 356/326 |
| 4,375,163 | 3/1983 | Yang .................................... 73/61.1 |
| 4,449,821 * | 5/1984 | Lee ..................................... 356/319 |
| 4,487,504 | 12/1984 | Goldsmith .......................... 356/323 |
| 4,519,706 | 5/1985 | Morley et al. ...................... 356/319 |
| 4,545,680 * | 10/1985 | Smith, Jr. ............................ 356/319 |
| 4,566,792 | 1/1986 | Suzuki ................................ 356/319 |
| 4,598,715 | 7/1986 | Mächler et al. ................ 356/326 X |
| 4,630,923 | 12/1986 | Tans et al. .......................... 356/301 |
| 4,660,974 | 4/1987 | Mächler et al. ................ 356/328 X |
| 4,663,961 | 5/1987 | Nelson et al. ........................ 73/24 |
| 4,678,277 | 7/1987 | Delhaye et al. .................... 356/301 |
| 4,685,801 | 8/1987 | Minekane .......................... 356/328 |
| 4,696,570 | 9/1987 | Joliot et al. ........................ 356/319 |
| 4,709,989 * | 12/1987 | Mächler ............................. 356/334 |
| 4,744,657 | 5/1988 | Aralis et al. ........................ 356/319 |
| 4,746,214 | 5/1988 | Akiyama et al. ................... 356/325 |
| 4,758,085 | 7/1988 | Lequime et al. ................... 356/319 |
| 4,804,266 | 2/1989 | Barshad ............................. 356/308 |
| 4,820,045 | 4/1989 | Boisde et al. ...................... 356/319 |
| 4,841,140 | 6/1989 | Sullivan et al. .................... 250/226 |
| 4,844,611 * | 7/1989 | Imahashi et al. ................... 356/246 |
| 4,866,265 | 9/1989 | Hohne ................................ 250/227 |
| 4,932,779 | 6/1990 | Keane ................................ 356/319 |
| 5,035,508 | 7/1991 | Carter et al. ....................... 356/416 |
| 5,116,123 | 5/1992 | Kurderer ........................... 356/326 |
| 5,131,746 | 7/1992 | O'Rourke et al. ................. 356/319 |
| 5,162,868 * | 11/1992 | Ando ................................. 356/326 |
| 5,210,590 * | 5/1993 | Landa et al. ....................... 356/319 |
| 5,212,537 * | 5/1993 | Birang et al. .................. 356/328 X |
| 5,231,461 * | 7/1993 | Silvergate et al. ................. 356/326 |

FOREIGN PATENT DOCUMENTS

| | | |
|---|---|---|
| 0228702 * | 7/1987 | (EP) . |
| 0254879 * | 2/1988 | (EP) . |

OTHER PUBLICATIONS

Church et al, "A Wide Spectral Range Ultra–Rapid Scan Spectrometer," Applied Optics, Feb. 1966, vol. 5, ™ 2 pp. 241–243.*

* cited by examiner

*Primary Examiner*—K. P. Hantis
(74) *Attorney, Agent, or Firm*—Harris Beach & Wilcox, LLP.

(57) ABSTRACT

A spectrometer includes a light source, a fiber optic bundle with a first and second leg, where the first leg has more fibers than the second leg, a flow cell, focusing optics, a disperser, and a detector. The spectrometer may also include a mask and system electronics to control the spectrometer. The spectrometer allows for simultaneous dual analysis of a reference and sample beam and minimizes errors and attenuations in the signals. The elimination of mechanical moving parts and control of attenuation losses enables less sophisticated control electronics to be utilized.

14 Claims, 3 Drawing Sheets

DOUBLE BEAM SPECTROMETER

FIELD OF THE INVENTION

This invention relates to optical instruments which provide analysis of materials, especially for chemical testing, such as blood analysis by means of spectrometry and, more particularly, to a dual beam spectrometer, without any moving parts, which enables simultaneous display and analysis of sample and reference beams with adjustments made for attenuation losses in the sample beam and for fluctuations in either beam.

The invention may be used in any spectropic system which performs chromatography. The preferred embodiment is used for high pressure liquid chromatography (HPLC). The improvements in spectrometry provided by the invention will be useful in other spectrometric instruments.

BACKGROUND OF THE INVENTION

Basically, a spectrometer is an optical device which uses a prism, diffraction grating or interferometer to separate light into its constituent parts. With a spectrometer, scientists and others are able to study matter by analyzing the spectrum produced by light passed through the matter. This has provided scientists and others with a powerful analytic tool. Unfortunately, limitations with spectrometers themselves have hindered the use of spectroscopy.

For example, many spectrometers utilize mechanically moving parts to control the transmission of light. These parts are subject to failure from repeated use and have inherent speed limitations. Additionally, spectrometers have traditionally lacked the ability to simultaneously display and analyze sample and reference beams. As a result, errors are often introduced by the sequential display and analysis. Even further, heretofore spectrometer have not effectively compensated for attenuation losses during display and analysis and have required complicated electronics and software to separate the desired signals from the noise in the detection systems.

SUMMARY OF THE INVENTION

It is a general object of the present invention to provide an improved spectrometer.

It is another object of the present invention to provide a spectrometer which compensates for attenuation losses.

It is a further object of the present invention to provide a spectrometer which improves signal to noise ratios enabling less expensive control electronics and software to be utilized.

According to the present invention, these and other objects and advantages are achieved in a dual beam spectrometer, without any moving parts, which includes a light source, a fiber optic bundle which splits into a first and second leg, with the first leg having more fibers than the second leg, a transmission cell positioned at the end of the first leg, focusing optics positioned at the end of the second leg and on the opposing side of the transmission cell, a dispersing device for separating the sample and reference beams into their constituent parts, and a detector for detecting the constituent parts.

The elimination of mechanical moving parts and the simultaneous display and analysis of sample and reference beams allows for high speed and repeated analysis suitable for commercial industries. Attenuation losses in the sample beams are compensated for with the differentiation in the number of fibers in the first and second legs. Further compensation for attenuation losses can be obtained by making the overall length of the second leg longer than the first leg and by tapering the transmission cell. The addition of mask filters between the dispersing device and the detector compensates for wavelength dependent source intensities, thereby improving the signal to noise ratio and allowing for the use of less sophisticated and expensive electronic control circuitry and software for processing and analyzing the data.

The spectrometer may be housed in a casing made from low thermal expansion material. The housing helps to minimize long-term drift caused by changes in ambient temperature.

BRIEF DESCRIPTION OF THE DRAWINGS

The foregoing and other objects, advantages and features of the invention and the best mode now known for practicing the invention will become more apparent from the accompanying drawings in which.

DETAILED DESCRIPTION OF THE INVENTION

Figure 1A:
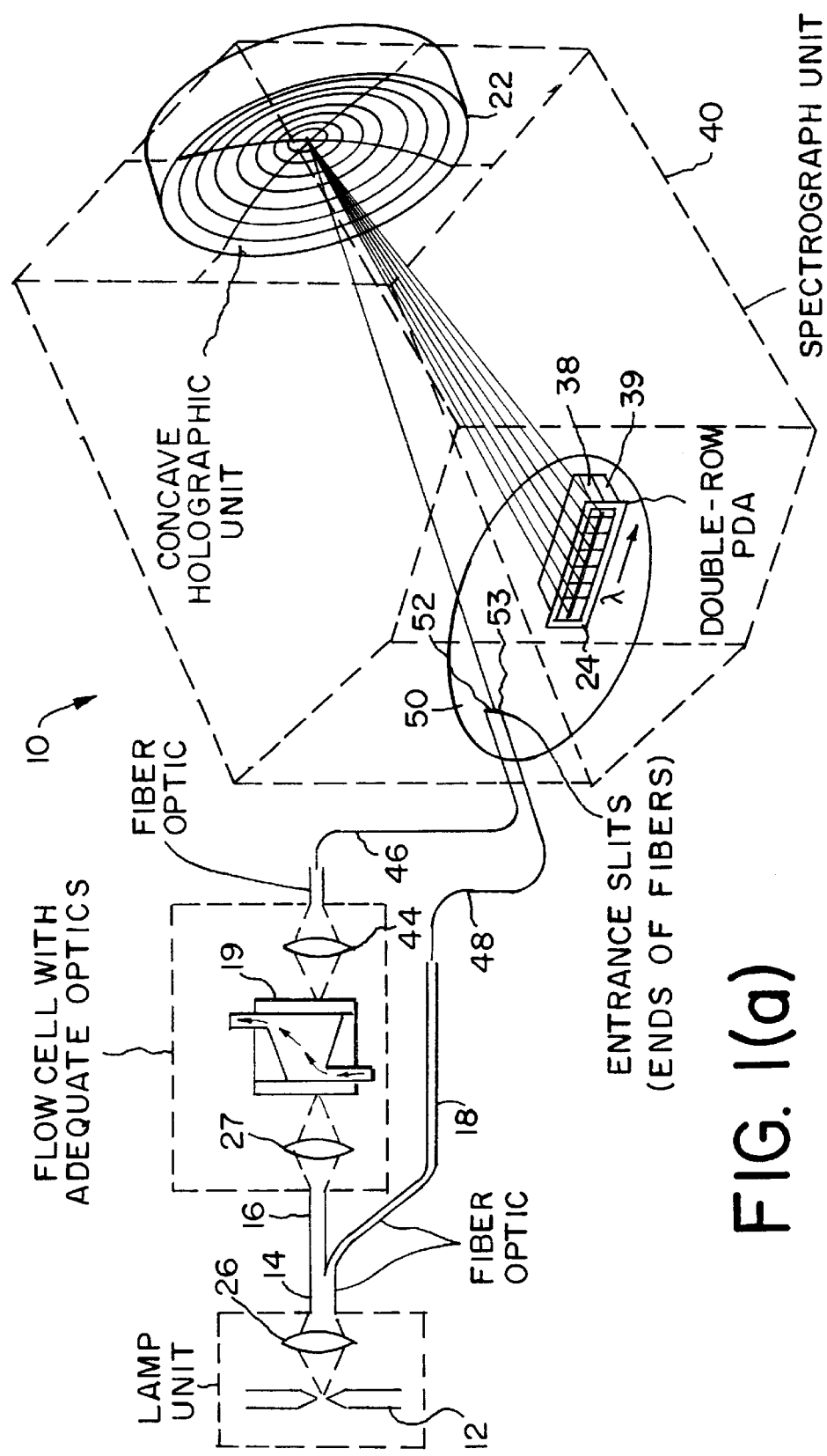
FIG. 1(a) is an exploded, schematic view of a double beam spectrometer, in accordance with the present invention.
Figure 1B:
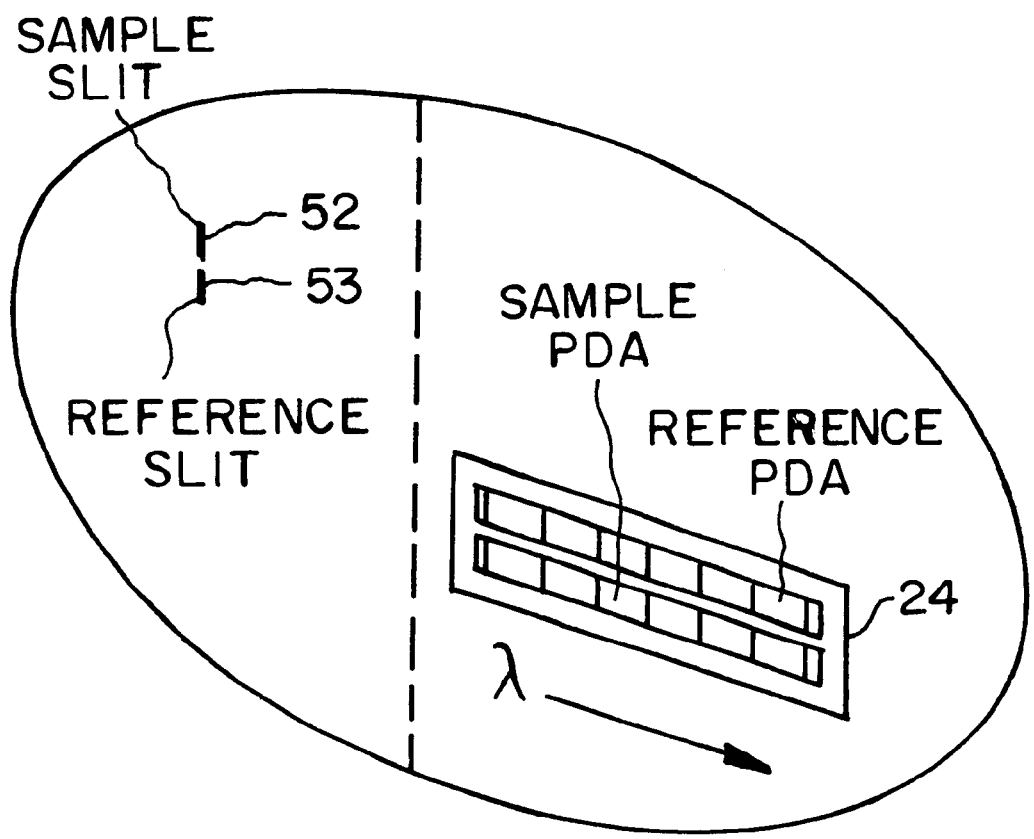
FIG. 1(b) is an enlarged fragmentary view of the slits and the photodiode array of the spectrometer shown in FIG. 1(a)

A double beam spectrometer 10 in accordance with the present invention is illustrated in FIGS. 1(a) and 1(b). The spectrometer includes a light source 12, a fiber optic bundle 14 which splits into a first and second leg 16 and 18, a transmission or flow cell 19, a focusing lens 44, a dispersing device 22, and a detector 24. The spectrometer 10 has no moving parts and is designed to compensate for attenuation losses in the light in the first leg 16 and to improve the signal-to-noise ratio of the detected portions of the light, thereby requiring less sophisticated and expensive control electronics and software.

Referring more specifically to FIG. 1(a), the light source 12 is preferably a deuterium or pulsed xenon source or an arc lamp, although other types of light sources could be used. For example, a super quiet L5257 manufactured by Hamamatsu could be used. The light source 12 provides a direct source of light to the fiber optic bundle 14 and is situated in the spectrometer for easy access. The light source 12 can be easily changed by the user with little or no alignment.

A focusing lens 26 may be positioned to focus light from the light source 26 onto one end of the fiber optic bundle 14. Preferably, the focusing lens 26 is made from quartz or Suprasil. Suprasil lens are available from Spindler and Hayer in Germany.

The fiber optic bundle 14 is positioned to receive light from the light source 12. Preferably, the fibers in the bundle 14 are disposed in a substantially random distribution. The random distribution of the fibers helps to avoid hot spots and light source wander inherent in source radiation. In this embodiment, Superguide G, manufactured by Fiberguide, is used for the fiber optic bundle 14, although other types of fiber optic cables could be used without departing from the scope of the invention.

The fiber optic bundle 14 splits into the first and second leg 16 and 18 with the first leg 16 having more fibers than the second leg 18. Preferably, the ratio of fibers in the first leg 16 to the second leg 18 is 10:1. The different ratio of fibers between the first and second legs 16 and 18 compensates for attenuation losses in the light in the first leg 16. To further compensate for attenuation losses, the second leg 18 may be made longer than the first leg 16. Preferably, the second leg 18 is approximately two times longer than the first leg 16.

A focusing lens 27 may be positioned between the end of the first leg 16 and transmission cell 19. The lens 27 helps to focus light into the cell 19 and may be made from material, such as quartz or Suprasil.

The transmission cell 19 is positioned to receive light from the end of the first leg 16. Preferably, the transmission cell 19 is a flow cell, such as a QS-113 produced by Hellma, although any type of transmission cell may be used. To minimize the effects of changes in refractive indices, the flow cell 19 may be tapered. As with the light source 12, the flow cell 19 is easily accessible within the spectrometer and can be replaced by the user with little or no alignment.

The focusing lens 44 is positioned on the opposing end of the transmission cell 19 from the end of the first leg 16 and focuses the sample beam onto one end of the first optical fiber 46. One end of the second optical fiber 48 is positioned to receive the reference beam from the end of the second leg 18. The other ends of the first and second fibers 46 and 48 are positioned in front of each of the vertically disposed sample and reference slits 52 and 53 in section 50. Preferably, the focusing lens is made from quartz or Suprasil, and Superguide G made by Fiberguide, is used for the first and second optical fibers 46 and 48, although other materials and fibers can be used without departing from the invention.

A casting 40 holds the dispersing device 22 and detector 24 and includes the section 50 with the slits 52 and 53. Although the casting 40 only houses the dispersing device 22 and detector 24 in this particular embodiment, the casting 40 can be made to house some or all of the parts of the spectrometer 10. The casting 40 may be made from ceramic or any other material with a low coefficient of thermal expansion to help minimize long term drift of the detector 24 as a result of changes in ambient temperature.

In this embodiment, the dispersing device 22 is a grating with a large number of narrow and substantially circular grooves placed side by side to diffract incident light into a spectrum. Preferably, a concave replicated holographic grating with 1,200 g/mm blazed at 250 nm is used. The device 22 disperses light at different angles depending on the wavelength of the light and the spacing of the grooves on the device 22. Although a grating is shown, a prism or filters could also be used in place of the grating. A grating has been chosen because light is more uniformly dispersed by a grating than a prism. Additionally, gratings with mirror material will reflect all wavelengths, while no current prism material is known which will transmit all wavelengths. The grating may be coated with $ALM_gF_2$ to maintain ultraviolet reflectivity.

In this embodiment, the detector 24 is a double-row PDA which has 512 by 2 pixels, such as the SQ-512Q available from Hamamatsu. Although a double-row PDA is shown, any type of detecting device may be used. The double-row PDA and the sample and reference slits 52 and 53 and are more clearly illustrated in the enlarged view of FIG. 1(b).

The spectrometer may also include a pair of suitable mask filters 38 and 39 positioned between the dispersing device 22 and the detector 24. Typically, the mask filters 38 and 39 are made from transmissive material and compensate for wavelength dependent source intensities and CCD inefficiencies. With the masks 38 and 39, the analysis and display of the incident light is easier, allowing for the use of simpler and less expensive electronics and software.

In this particular embodiment, the spectrometer operates when the light source 12 is pulsed to produce a light which impinges on the focusing lens 26. The focusing lens 26 focuses the light onto one end of the fiber optic bundle 14. The light in the bundle 14 is guided down the first and second legs 16 and 18 splitting into a sample and a reference beam. A lens 27 located at the end of the first leg 16 focuses the sample beam emerging from the leg 16 onto the transmission cell 19.

The difference in the number of optical fibers in the first and second legs 16 and 18, the difference in the length of the first and second legs 16 and 18, and the tapered flow cell 19 all help to compensate for attenuation losses in the sample beam.

The sample beam from the transmission cell 19 is focused by the lens 44 onto one end of the optical fiber 46. The reference beams in the second leg 18 is transmitted to the one end of the second optical fiber 48. The first and second optical fibers 46 and 48 guide the sample and reference beams to the sample and reference slits 52 and 53. The beams pass through the slits 52 and 53 and are diffracted by the dispersing device 22.

The dispersing device 22 separates the sample and reference beams into their constituent wavelength parts. Both the diffracted sample and reference beams pass through the mask filters 38 and 39 and strike the detector 24. The mask filters 38 and 39 compensate for wavelength dependent source intensities. As a result, the signal to noise ratio is improved as much as 40%. The higher signal to noise ratio enables the spectrometer 10 to use less sophisticated control electronics and software. The device 24 accumulates charge for a predetermined amount of time and is then read out and analyzed as will be explained in greater detail with the description of FIG. 2.

Figure 2:
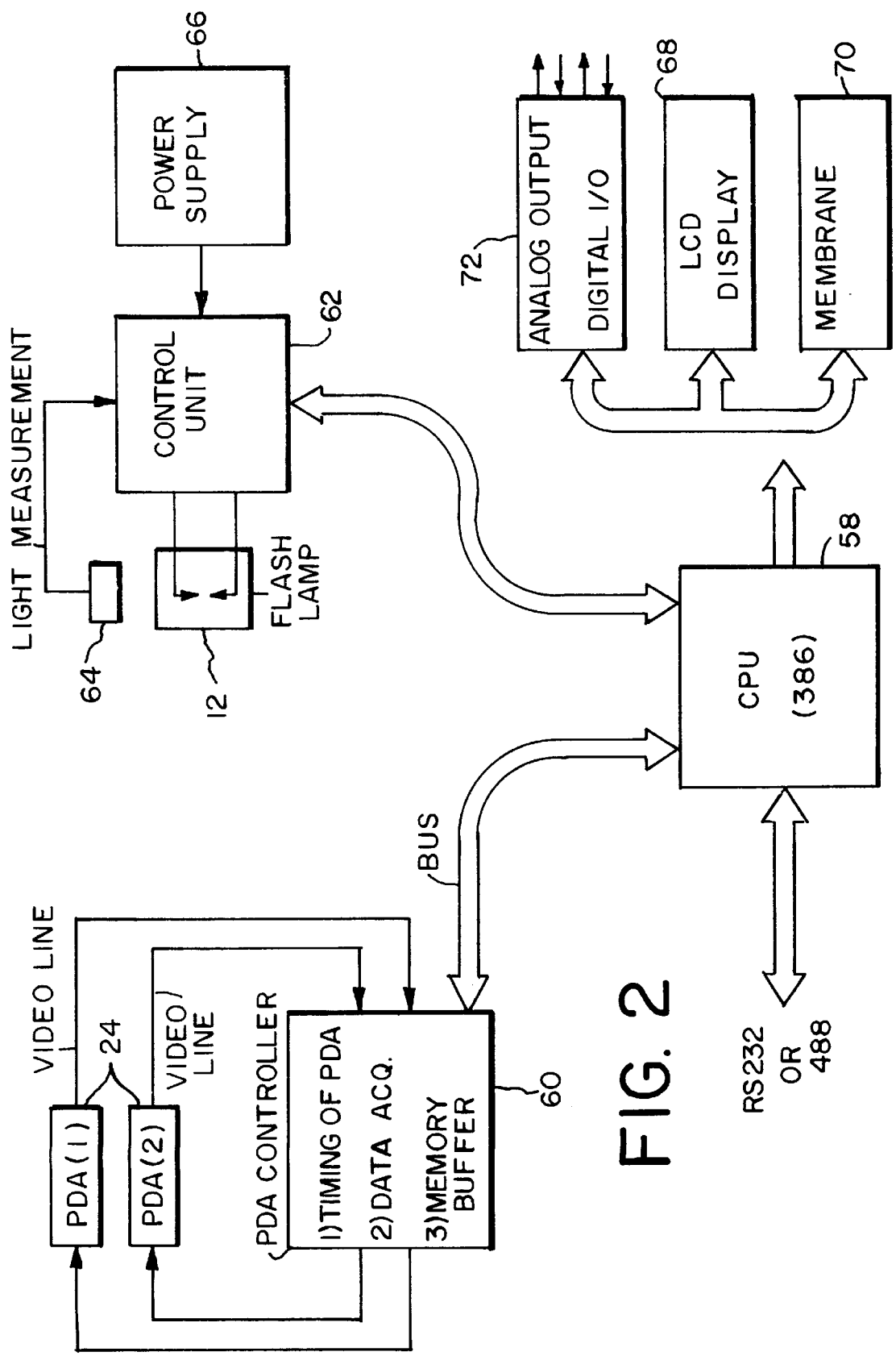
FIG. 2 is a block diagram of the system electronics used in conjunction with the spectrometer shown in FIG. 1.

Referring to FIG. 2, the dual beam spectrometer in FIGS. 1(a) and 1(b) is operated by a digital processing unit, such as a microprocessor or central processing unit (CPU) 58. The CPU 58 is connected to a PDA controller 60 and a control unit 62. The PDA controller 60 is coupled to the detector 24 and the control unit 62 is coupled to the light source 12 (e.g., a xenon flash lamp), a light measuring device 64 and a power supply 66. The CPU 58 may be connected to an LCD display 68, keyboard 70 and/or analog output or digital output 72. Although an LCD display device is shown, any type of display device may be used, such as PC monitor. A typical sequence of operations of the spectrometer 10 control system is as follows.

The microprocessor 58 controls the PDA controller 60 and control unit 62 according to the particular software program loaded into the spectrometer 10, such as lab calculations by Galactic. In response to control signals from the CPU 58, the PDA controller 60 controls the timing of the accumulation of data and controls when the data is retrieved from the detector 24, which in this embodiment is a PDA array. The data read out by the PDA controller 60 is typically stored in a memory buffer in the PDA controller 60 before being sent to the microprocessor 58. The CPU 58 stores and processes the received data according to the particular instructions in the software and transmits the processed data out via the analog output or digital output 72 or to the display 68.

The control unit 62 also operates in response to control signals from the CPU 58 and from inputs from the light measuring device 64, which measures the light output by the light source 12. The control unit 62 adjusts the light output of the light source 12, in response to these inputs. The control unit 62 is powered by the power supply 66.

Having thus described the basic concept of the invention, it will be readily apparent to those skilled in the art that the foregoing detailed disclosure is intended to be presented by way of example only, it is not limiting. Various alterations, improvements and modifications will occur and are intended to those skilled in the art, those not expressly stated herein. These modifications, alterations and improvements are intended to be suggested hereby, and are within the spirit and scope of the invention. Accordingly, the invention is limited only by the following claims and equivalents thereto.

What is claimed:

1. A spectrometer comprising:

a light source;

a fiber optic bundle which splits into a first leg and a second leg, with said first leg having more fibers than said second leg and with one end of said fiber optic bundle positioned to receive light from said light source which is guided down said first and second legs as first and second light beams, respectively;

transmissive means for holding a sample, with said transmissive means positioned to receive the first light beam output by the end of said first leg;

means for dispersing the first and second light beams;

means for focusing the first and second light beams output from said transmissive means and said second leg, respectively, onto said means for dispersing;

means for simultaneously detecting the first and second light beams from said means for dispersing; and means for reading data from said means for detecting.

2. The spectrometer as recited in claim 1 wherein said second leg is longer than said first leg and said second leg has a length sufficient to compensate for attenuation losses in said first leg.

3. The spectrometer as recited in claim 1 further comprising at least one mask positioned between said means for dispersing and said means for detecting.

4. The spectrometer as recited in claim 2 wherein the fibers in said fiber optic bundle are disposed in a substantially random distribution.

5. The spectrometer as recited in claim 3 wherein said transmissive means is a flow cell.

6. The spectrometer as recited in claim 5 wherein said flow cell is tapered.

7. The spectrometer as recited in claim 6 wherein said means for reading comprises:

a controller which controls when data is read from said means for detecting;

a buffer memory in said controller for storing data read from said memory; and a central processing unit coupled to said controller.

8. The spectrometer as recited in claim 7 further comprising:

a light measuring device;

a power supply; and a control unit coupled to said light source, said measuring device, said power supply and said central processing unit, with said control unit adjusting the light output by said light source in response to the light measured by said measuring device.

9. The spectrometer as recited in claim 8 further comprising a focusing lens for focusing light output from said light source on one end of said fiber optic bundle.

10. The spectrometer as recited in claim 9 wherein said means for dispersing is a diffraction grating.

11. The spectrometer as recited in claim 10 wherein said means for detecting is a photodiode array.

12. The spectrometer as recited in claim 11 further comprising a housing constructed from low thermal expansion material.

13. The spectrometer as recited in claim 12 wherein said housing is made from ceramic.

14. The spectrometer as recited in claim 3 wherein the fibers in said fiber optic bundle are disposed in a substantially random distribution.

* * * * *